US005876956A

United States Patent [19]
Jones et al.

[11] Patent Number: 5,876,956
[45] Date of Patent: Mar. 2, 1999

[54] METHODS FOR IDENTIFICATION OR PURIFICATION OF CELLS CONTAINING AN ENZYMATIC INTRACELLULAR MARKER

[75] Inventors: Richard J. Jones, Bel Air; O. Michael Colvin, Baltimore; John Hilton, Parkton; Saul Sharkis, Towson, all of Md.

[73] Assignee: Johns Hopkins University School of Medicine, Baltimore, Md.

[21] Appl. No.: 440,656

[22] Filed: May 15, 1995

[51] Int. Cl.⁶ .................................................. C12Q 1/32
[52] U.S. Cl. ................................ 435/26; 435/29; 435/372
[58] Field of Search ............................... 435/7.21, 26, 29, 435/240.2, 240.21, 269, 355, 372, 372.2, 372.3

[56] References Cited

U.S. PATENT DOCUMENTS

| | | | |
|---|---|---|---|
| 4,714,680 | 12/1987 | Civin | 435/240.25 |
| 4,965,204 | 10/1990 | Civin | 435/240.27 |
| 4,999,291 | 3/1991 | Souza | 435/69.1 |
| 5,035,994 | 7/1991 | Civin | 435/2 |
| 5,061,620 | 10/1991 | Tsukamoto et al. | 435/7.21 |
| 5,081,030 | 1/1992 | Civin | 435/240.2 |
| 5,087,570 | 2/1992 | Weissman et al. | 435/240.1 |
| 5,132,242 | 7/1992 | Cheung | 436/501 |
| 5,137,809 | 8/1992 | Loken et al. | 435/2.21 |
| 5,196,315 | 3/1993 | Ronnett et al. | 435/29 |
| 5,256,560 | 10/1993 | Lawman et al. | 435/240.2 |
| 5,290,684 | 3/1994 | Kelly | 435/29 |
| 5,385,822 | 1/1995 | Melnicoff et al. | 435/5 |
| 5,399,493 | 3/1995 | Emerson et al. | 435/172.3 |
| 5,464,753 | 11/1995 | Chaudhary et al. | 435/7.24 |
| 5,525,461 | 6/1996 | Rittershaus | 435/5 |

OTHER PUBLICATIONS

Rotman, et al., Membrane Properties of Living Mammalian Cells as studied by Enzymatic Hydrolysis of Fluorogenic Esters, *Biochemistry: Rotman and Papermaster , Proc. N.A.S.*, vol. 55, pp. 134–140, 1966.

Hilton, John, role of Aldehye Dehydrogenase in Cyclophosphamide–resistant L 1210 Leukemia[1], *Cancer Research vol. 44*, pp. 5156–5160, Nov. 1984.

Gordon, et al., 4–Hydroperoxycyclophoshamide Inhibits Proliferation By Human Granulocytemacrophage Colony–Forming Cells (GM–CFC) But Spares More Primitive Progenitor Cells, *Leukemia Research vol. 9, No. 8*, pp. 1017–1021, 1985.

Kohn, et al., Effect of Aldehyde Dehyrogenase Inhibitors on the ex Vivo Sensitivity of Human Multipotent and Commited Hematopoietic Progenitor Cells and Malignant Blood Cells to Oxazaphosphorines, *Cancer Research 47*, 3180–85, 87.

Sahovic, et al., Role for Aldehyde Dehydrogenase in Survival of Progenitors for Murine Blast Cell Colonies after Treatment with 4–Hydroperoxycyclophophamide in Vitro[1], *Cancer Research 48*, 1223–1226, Mar. 1, 1988.

Kastan, et al., Direct Demonstration of Elevated Aldehyde Dehydrogenase in Human Hematopoietic Progenitor Cells, *Blood*, vol. 75, No. 10, (May 15), pp. 1947–1950, 1990.

Russo, et al., The Role of Aldehyde Dehydrogenase Isozymes in Cellular Resistance to the Alkylating Agent Cyclophosphamide, *Enzymology and Molecular Biology of Carbonyl Metabolism 2*, pp. 65–79, 1989.

Kastan M., Direct Demonstration of Elevated Aldehyde Dehydrogenase in Human Hematopoietic Progenitor Cells, Bllod 75(10) 1947–1950, May 1990.

Orlic, D., Purification and Characterization of Heterogeneous Pluripotent Hematopoietic Stem Cell Populations Expressing High Levels of c–kit Receptor, Blood 82(3) 762–770, Aug. 1993.

Neben, et al. "Short– and Long–term Repopulation of Lethally Irradiated Mice by Bone Marrow Stem Cells Enriched on the Basis of Light Scatter and Hoechst 33342 Fluorescence", Experimental Hematology, 19:958–967, 1991.

Pincus, et al. "Dansyl Cadaverine: A Fluorescent Probe and Marker in Cell Membrane Studies", Archives of Biochemistry and Biophysics, 169:724–730, 1975.

Sato, et al. Expression and Factor–Dependent Modulation of the Interleukin–3 Receptor Subunits on Human Hematopoietic Cells, Blood, 82:752–761, 1991.

Biederbick, et al. "Monodansycadaverine (MDC) is a specific in vivo marker for autophagic vacuoles", European Journal of Cell Biology, 66:3–14, 1995.

*Primary Examiner*—Ralph Gitomer
*Attorney, Agent, or Firm*—Fish & Richardson P.C.

[57] ABSTRACT

Production of a stem cell enriched cell composition using essentially non-toxic methodology comprising contacting a cell mixture with a cell-permeable, fluorescent non-polar compound that reacts upon contact with intracellular enzyme aldehyde dehydrogenase or phosphokinase found substantially exclusively in stem cells so as to form a biocompatible fluorescent product that is polar and non-permeable to the membrane of the stem cells, and isolating the cells containing the marker by fluorescent cell sorting.

5 Claims, 3 Drawing Sheets

METHODS FOR IDENTIFICATION OR PURIFICATION OF CELLS CONTAINING AN ENZYMATIC INTRACELLULAR MARKER

STATEMENT AS TO FEDERALLY SPONSORED RESEARCH

This invention was partially supported by NIH Grants # PO1 CA15396 and RO1 HL46533. The United States Government may have an interest in the subject matter of this invention.

FIELD OF THE INVENTION

This invention relates generally to enriched pluripotent stem cell compositions, methods and compounds for producing these populations, and the use of these compositions in the treatment of various disorders in which hematopoietic reconstitution is desirable, such as by bone marrow transplantation (BMT).

BACKGROUND OF THE INVENTION

All the cells circulating in the blood are descendants of a very small number of pluripotent stem cells. These ancestral cells, which comprise less than 0.01 percent of the nucleated cells in the bone marrow, are capable of restoring normal hematopoiesis in individuals in need of reconstitution of their bone marrow. The pluripotent stem cell has the unique capacity for self-renewal and the potential for growth and differentiation along granulocytic, monocytic, erythroid, megakaryocytic, and lymphoid lineages. Some stem cells divide and give rise to progeny that lose their ability to differentiate along multiple pathways and become committed to a specific hematopoietic lineage. These committed progenitor cells continue to proliferate and differentiate into morphologically identifiable precursor cells which then undergo terminal maturation, thereby developing highly specialized functions and lose their ability to proliferate. Techniques have been developed which support the growth and differentiation of hematopoietic progenitor cells in vitro. Using these techniques, hematopoietic colonies of mixed and single lineages have been identified and characterized with respect to the factors required for their growth.

Mammalian blood cells provide for an extraordinarily diverse range of activities. The blood cells are divided into several lineages based on function. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes, as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

As noted above, the stem cell population constitutes only a small percentage of the total number of leukocytes in bone marrow. At the present time it is not known how many of the markers associated with differentiated cells are also present on the stem cell. One marker which has been indicated as present on stem cells, CD34, is also found on a significant number of lineage-committed progenitors. Another marker that provides for some enrichment of progenitor activity is Class II HLA (particularly a conserved DR epitope recognized by a monoclonal antibody designated J1-43). However, these markers are found on numerous lineage-committed hematopoietic cells. In particular, B cells (CD19+) and myeloid cells (CD33+) make up 80–90% of the CD34+ population. Moreover, a combination of CD 3, 8, 10, 15, 19, 20 and 33 will mark $\leq 90\%$ of all CD34+ cells. Therefore, in view of the small proportion of the total number of cells in the bone marrow which are stem cells, the uncertainty of the markers associated with stem cells, as distinct from more differentiated cells, and the general inability to conduct a definitive biological assay for human stem cells, the identification and purification of stem cells has been elusive.

Aldehyde dehydrogenase (ALDH) is an enzyme responsible for oxidizing intracellular aldehydes and plays an important role in metabolism of ethanol, vitamin A, and cyclophosphamide. Substrates for these enzymes include acetaldehyde and biogenic amines produced during catecholamine catabolism. Further, ALDH appears to be a crucial step in the conversion of vitamin A to its active metabolite, retinoic acid (J. Labrecque, et al, *Biochem Cell Biol,* 71:85, 1993; A. Yoshida, el al., *Enzyme*, 46:239, 1992). Of the four ALDH isozymes identified (A. Yoshida, et al., *Enzyme,* 46:239, 1992), liver cytosolic ALDH appears to be the specific isozyme involved in metabolism of vitamin A (J. Labrecque, et al., *Biochem Cell Biol,* 71:85, 1993; A. Yoshida, et al., *Enzyme,* 46:239, 1992) and cyclophosphamide resistance (J. E. Russo et al., *Cancer Res* 48:2963, 1988). Both hematopoietic progenitors and intestinal crypt stem cells display high levels of cytosolic ALDH, and are accordingly relatively resistant to cyclophosphamide. Although all hematopoietic progenitors are known to express relatively high levels of cytosolic aldehyde dehydrogenase, both mouse and human HSC appear to express significantly higher levels than less primitive hematopoietic progenitors. Primitive hematopoietic progenitors are more resistant to 4HC than are later progenitors, and this appears to result in large part from their high expression of cytosolic ALDH rather than from their non-cycling status. However, there is no difference in the sensitivity to 4HC analogues of primitive hematopoietic progenitors that are not inactivated by aldehyde dehydrogenase (E. A. Sahovic et al., *Cancer Res,* 48:1223, 1988).

Increased AND-dependent aldehyde dehydrogenase (ALDH, Enzyme Commission 1.2.1.3) activity has been identified as a mechanism of antitumor drug resistance to the alkylating agent cyclosphosphamide (CPA). CPA, a nitrogen mustard derivative incorporating an oxazaphosphorine, is a prodrug, requiring activation by the cytochrome P-450 mixed function oxidase system to produce 4-hydroxycyclophosphamide (4HC). A spontaneous beta elimination from aldophosphamide liberates the active DNA alkylating agent, phosphoramide mustard, plus acrolein.

CPA is currently used clinically in the treatment of a diverse group of solid and hematologic malignancies, and is a key component of the cytoreductive regimens prior to bone marrow transplantation. A major factor in the success of CPA has been the high therapeutic index observed (Mullins and Colvin, *Cancer Chemother Repts,* 59:411, 1975). This high therapeutic index is due in part to a "sparing" effect that CPA exerts on normal hematopoietic stem cells (Fried, et al., *Cancer Research,* 37:1205, 1977) and intestinal crypt stem cells. While damage to these rapidly proliferating stem cell renewal systems is the dose-limiting toxicity of other alkylating agents, these tissues are not profoundly effected by CPA. The diminished toxicity is specific for CPA (and its activated congeners) among alkylating agents. Thus, elevated ALDH levels have been postulated as a mechanism for the relative resistance of bone marrow and intestinal stem cells to CPA. In vivo studies in mice have shown that a cytosolic ALDH isozyme found in murine tumor tissue is responsible for conferring cyclophosphamide resistance (J. E. Russo et al., *Enzymology and Molecular Biology of Carbonyl Metabolism*, 2:65–79, 1989).

Elevated levels of ALDH have been best characterized as a mechanism of cellular resistance to CPA in the L1210 murine lymphocytic leukemia model (DeWys, 1973), in which a 200-fold higher cytosolic ALDH activity was measured in the cell line resistant to CPA (L1210/CPA) compared to the sensitive, wild-type line.

By definition human hematopoietic stem cells (HSC) are progenitor cells and are pluripotent in that they have the ability to repopulate lymphohematopoietic lineages on a long-term basis. The isolation of human HSC remains a goal particularly difficult to achieve, since prior to the present invention no single cell characteristic has been found specific for HSC which could be used to prepare an enriched cellular composition. Therefore, the isolation and/or identification of HSC suitable for re-introduction into a host requires an eventual in vivo approach, yet prior art techniques for HSC detection, namely measurement of substrate oxidation in whole cell lysates (J. E. Russo et al., *Cancer Res* 48:2963, 1988; J. E. Russo et al., *Enzymology and Molecular Biology of Carbonyl Metabolism* 2:65–79, 1989) or reaction of fixed cells with antibodies (M. B. Kastan et al., *Blood* 75:1947, 1990; J. E. Russo et al., *Enzymology and Molecular Biology of Carbonyl Metabolism* 2:65–79, 1989) are lethal to the cells being studied. By the same token, the applicability of animal models has been limited because analogues of many well-characterized HSC markers have not been identified in other species (G. J. Spangrude et al., *Science,* 241:58, 1988; C. T. Jordan, et al., *Cell,* 61:953, 1990). Thus, there is a need for a stem cell enriched composition which is produced using essentially non-toxic methodology thereby allowing safe and effective reconstitution of a host in need of such therapy. The present invention answers this need.

SUMMARY OF THE INVENTION

Recognizing the importance of an enriched stem cell composition, the inventors developed a method and compounds for producing a pluripotent stem cell composition which can be used as an in vivo source of hematopoietic cell lineages in reconstitutive therapy. This composition advantageously provides a heretofore unattained percentage of uncommitted stem cells which are isolated under essentially non-toxic conditions to thereby enhance the utility of the composition for therapeutic purposes.

BRIEF DESCRIPTION OF THE DRAWINGS

FIGS. 1A and 1B are scans showing dansyl fluorescence from four leukemia cell lines treated with densylaminoacetaldehyde (DAAA). These results are from one representative experiment of human leukemia cell lines treated with DAAA. Gray peaks represent unstained cells and black peaks represent stained cells.

FIG. 4A shows the results obtained with human leukemia cells, and FIG. 4B shows the results obtained with mouse leukemia cell lines.

DESCRIPTION OF THE PREFERRED EMBODIMENTS

Figure 1A:
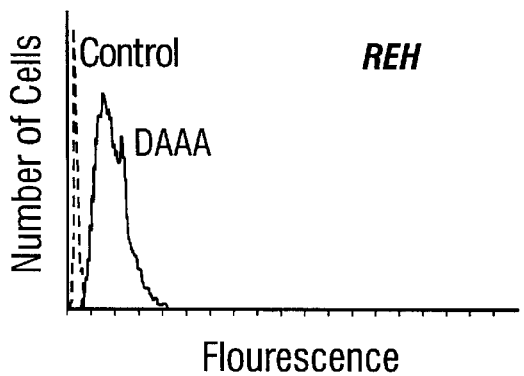
FIGS. 1A–D are scans showing dansyl fluorescence from cells treated with dansylaminoacetaldehyde.
Figure 1B:
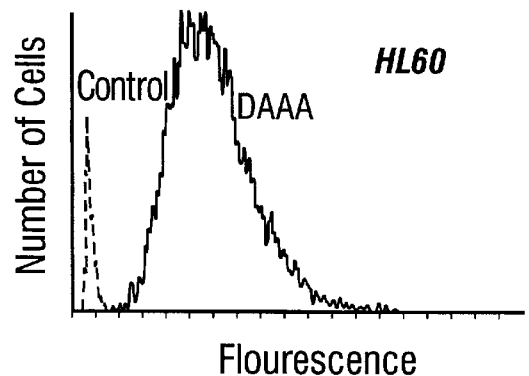
Figure 1C:
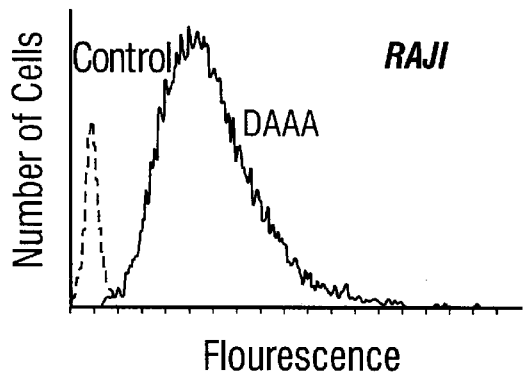
Figure 1D:
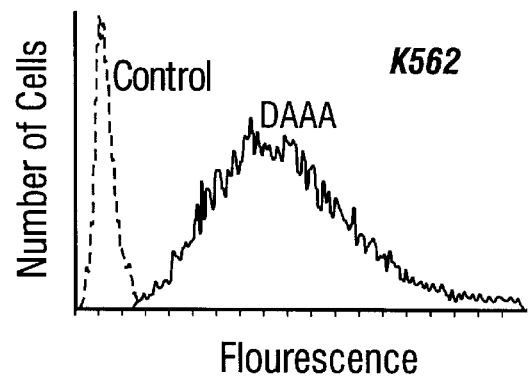

In one embodiment, the present invention provides a method for indirectly identifying intact, viable cells within a cell mixture that express an intracellular marker, for instance an enzyme such as cytosolic ALDH. The intracellular marker reacts with a cell-permeable fluorescent aldehyde to render the fluorescent aldehyde polar, and, hence, non-permeable to the cell membrane. Accordingly, the method of this invention comprises the steps of contacting a cell mixture with a cell-permeable, non-polar fluorescent aldehyde that is rendered polar by contact with the intracellular marker, for instance by oxidation. Once rendered polar, the fluorescent aldehyde is no longer permeable to the cell membrane and, hence, is trapped within only those cells in the cell mixture that express the intracellular marker. Cells containing the trapped polar, non-permeable fluorescent aldehyde so formed are identified by fluorescence using techniques and equipment well known to those of skill in the art. Cell populations enriched in cells containing the polar fluorescent aldehyde can be obtained using cell sorting techniques, preferably automated fluorescence cell sorting techniques that separate cells containing or having attached thereto a fluorescent marker, such as Fluorescence Activated Cell Sorting (FACS). Such fluorescence cell sorting techniques are well known to those of skill in that art and do not form a part of this invention.

In the preferred embodiment, the fluorescent cell permeable aldehyde is a substrate for aldehyde dehydrogenase (ALDH), and is oxidized by contact with intracellular ALDH to a non-permeable polar fluorescent molecule. When the fluorescent polar molecule is contacted by a light beam having the requisite wavelength to excite the molecule, the fluorescent light emitted as the molecule drops back to its ground state is detected, thereby indicating the presence of a cell or cell population containing intracellular ALDH. Most preferably, the fluorescent aldehyde is the novel compound, dansylaminoacetaldehyde (DAAA), a substrate for aldehyde dehydrogenase, or analogs thereof. Dansyl fluorescence is excited at both 351.1 nm and 363.8 nm and is detected at about 521 nm. A description of the synthesis of this novel compound is found in Example 2 of this application. Alternatively, the method of this invention can be used to detect intracellular phosphokinases. For example, 2-deoxy-2-dansylaminoglucose (2,2-DDG) should be a fluorescent substrate for hexokinase (a phosphokinase). Phosphorylation of this compound by hexokinase will produce phosophorylated glucose (dansylaminoglucose-6-phosphate) which will be trapped in the cell. Thus, 2,2-DDG would represent a reagent to detect the presence of hexokinase in cells.

Fluorescent cell permeable and non-polar derivatives of DAAA have also been synthesized and are contemplated within the scope of this invention. For instance, dansyl aminoacetaldehyde diethyl acetal is a non-polar DAAA precursor that can be converted to DAAA by exposure to acid before being exposed to cells. Alternatively, fluorescent derivatives of naturally occurring aldehydes can also be used in the practice of this invention. For instance, a fluorescent derivative of retinaldehyde can be synthesized and used to identify cells active in retinoic acid synthesis.

The general method for producing a non-polar fluorescent aldehyde for use in the practice of this invention, i.e., a substrate for aldehyde dehydrogenase, is by reacting a physiologically compatible fluorescent molecule bearing an electrophilic group and a protected aldehyde, such as a methyl or ethyl acetal having a nucleophilic group. For example, the fluorescent electrophile may be a sulfonyl chloride, such as dansyl chloride or Texas Red sulfonyl chloride; an isothiocyanate, such as fluorescein isothiocyantate; an N-hydroxysuccinimide, such as N-hydroxy succinimidorhodamine; or a thiol-reactive fluorescent derivative, such as 5-iodoacetamidofluorescein. The protected aldehyde may contain one of a number of nucleophilic groups, such as an amino, hydroxyl, phenolic, or thiol group. The teachings of the art regarding fluorescent compounds are well known.

In another embodiment, the method for identifying cells containing cytosolic ALDH in intact, viable cells is used as a technique for providing a composition enriched in hematopoietic stem cells, preferably a cell suspension of pluripotent hematopoietic stem cells (pluripotent HSC), that is substantially free of lineage-committed cells. By definition "pluripotent" hematopoietic stem cells are those progenitor cells having the ability to repopulate lymphohematopoietic lineages on a long-term basis.

Optionally, a large proportion of differentiated cells may be removed by initially using a "relatively crude" separation. The source of the cells may be the bone marrow, fetal, neonate, or adult or other hematopoietic cell source, e.g., fetal liver or blood. For example, magnetic bead separations may be used initially to remove large numbers of lineage committed cells, namely major cell populations of the hematopoietic systems, including such lineages as T cells, B cells (both pre-B and B cells), myelomonocytic cells, or minor cell populations, such as megakaryocytes, mast cells, eosinophils and basophils. Preferably, at least about 70%, usually at least 80%, of the total hematopoietic cells will be removed. It is not essential to remove every dedicated cell class, particularly the minor population members at the initial stage. Usually, however, the platelets and erythrocytes will be removed prior to fluorescence sorting. Since there will be positive selection in the protocol, the dedicated cells lacking the positively selected marker will be left behind. However, it is preferable that negative selection is done for all of the dedicated cell lineages, so that in the final positive selection, the number of dedicated cells present is minimized.

The methods of this invention have therapeutic utility. For instance, the suspension of HSC and/or pluripotent HSC obtained by the method of this invention can be used for performing hematopoietic reconstitution of a recipient using an enriched pluripotent HSC composition derived from the recipient (autologous reconstitution) or derived from an individual other than the recipient (non-autologous reconstitution) in the treatment or prevention of various diseases or disorders such as anemias, malignancies, autoimmune disorders, and various immune dysfunctions and deficiencies, as well as recipients whose hematopoietic cellular repertoire has been depleted, such as recipients treated with various chemotherapeutic or radiologic agents, or recipients with AIDS. Other therapeutic uses of the compositions of the invention are well known to those of skill in the art.

Since high levels of cytosolic ALDH produce cyclophosphamide-resistance in certain tumor cell lines, in another embodiment the method of the present invention for identifying cells containing cytosolic ALDH can be used to study the phenomenon of cyclophosphamide resistance in tumor cells. Further, the methods of this invention can be used to recover and study subpopulations of viable cells from a cell mixture, such as a bone marrow aspirate, containing leukemia cells or other malignant cells.

In yet another embodiment of the invention, the method of providing a substantially homogeneous composition of human pluripotent hematopoietic stem cells (pluripotent HSC) can be used to separate the progenitor stem cells useful in a bone marrow transplant from the other healthy cells in a bone marrow aspirate provided by a healthy bone marrow donor. Alternatively, when the donor is the patient, the method of this invention can be used prior to treatment of the patient with chemotherapeutic or radiologic agents, to separate the pluripotent HSCs for eventual reintroduction into the patient after therapy has been completed. In the latter case, the tumor cells can be removed from the cell mixture comprising the bone marrow aspirate by tagging the tumor cells with markers that are independent of the intracellular aldehyde-derived fluorescence described, such as tumor-specific cell surfaces markers. One skilled in the art will appreciate that alternative methods well known in the art, such as ex vivo magnetic cell sorting can also be employed to remove the tumor cells from the cell mixture before subjecting the cell mixture to cell sorting utilizing the intracellular fluorescent aldehyde method of this invention.

In another aspect, the invention also provides an enriched cellular composition of human lymphohematopoietic stem cells (pluripotent HSC), believed to be the earliest lymphohematopoietic stem cell (pluripotent HSC). The term "substantially homogeneous" as used herein means that the composition contains no more than about 5% of lineage-committed cells. The pluripotent HSC are phenotypically and biologically distinct from the pluripotent HSC described by others and characterized by the following attributes: (a) having a small size, generally from about 8 to 10 $\mu$m; (b) expressing levels of ALDH from about 10 to about 30 nanomoles aldehyde oxidized/mg protein/min; (c) being substantially free from expression of markers specific for committed lymphohematopoietic lineages, such as CD19, CD33 and CD5; and (d) being negative for expression of c-kit and Thy. Preferably, no more than about 30% of the cells in the enriched cellular composition express CD34, as determined by flow cytometry using anti-CD34 antibody. As a result, the use of CD34, c-kit and Thy as markers for the identification and isolation of the pluripotent HSC cells herein is precluded. This analogous cell population in the mouse has been shown to be the pluripotent HSC. 5–10 of these marrow cells (small, lineage-negative, ALDH$^+$) will reconstitute all bone marrow-derived lineages of a mouse for the life-time of the mouse. These cells are also capable of extensive self-renewal as shown by their ability to continue to reconstitute all bone marrow-derived cells upon serial bone marrow transplantation.

The substantially homogeneous composition of human lymphohematopoietic stem cells provided herein is capable of self-regeneration in a coculture medium. Exemplary methods for expansion and/or providing for the optimization of human hematopoietic progenitor cell cultures are known in the art, for instance, in U.S. Pat. No. 5,399,493, which is incorporated herein by reference in its entirety. As one skilled in the art will also appreciate, the pluripotent HSCs of this invention can be directed to differentiation as a lymphoid, myeloid, or erythroid-lineage population by incubation with the appropriate hematopoietic growth factor or combination of growth factors. Representative growth factors known in the art that can be used for these purposes are IL-1, IL-6, SCF, EPO, and IL-3. Other growth factors for stimulating proliferation of hematopoietic lineages from the stem cell composition of the invention are known to those of skill in the art (see, for example, Harrison's Principles of Internal Medicine, Isselbacher, et al., eds., pp 1714–1717, McGraw Hill, 1994, incorporated herein by reference). As used herein, the term "a suitable hematopoietic growth factor" means one or more hematopoietic growth factors known in the art to direct a progenitor stem cell to the desired lymphoid, granulocytic, monocytic, megakaryocytic, myeloid, or erythroid-lineage cell population.

The human stem cells provided herein find a number of uses, for instance: (1) in regenerating the hematopoietic system of a host deficient in stem cells; (2) in treatment of a host that is diseased and can be treated by removal of bone marrow, isolation of stem cells, and treatment of the host with therapeutic agents such as drugs or irradiation prior to re-engraftment of stem cells; (3) as a progenitor cell population for producing various hematopoietic cells; (4) in detecting and evaluating growth factors relevant to stem cell self-regeneration; and (5) in the development of hematopoietic cell lineages and screening for factors associated with hematopoietic development.

The enriched cellular composition of human lymphohematopoietic stem cells provided herein can be obtained by isolating cells that express an intracellular enzyme which hydrolyzes a fluorescent non-polar substrate. Preferably, the enzyme is ALDH and the substrate is DAAA as described in the Examples herein. In a preferred embodiment of the method of the invention, therefore, the cell sorting step is performed using automated cell sorting, such as fluorescence activated cell sorting (FACS), a high speed method of sorting fluorescent cells.

The following examples illustrate the manner in which the invention can be practiced. It is understood, however, that the examples are for the purpose of illustration and the invention is not to be regarded as limited to any of the specific materials or conditions therein.

EXAMPLE 1
Synthesis of N-dansyl aminoacetaldehyde (DAAA).

DAAA diethyl acetal was synthesized by adding triethylamine (28 $\mu$L, 0.2 mmol) and then aminoacetaldehyde diethyl acetal (29 $\mu$L, 0.2 mmol, Sigma Chemical Co.) via syringe to a solution of dansyl chloride (54 mg, 0.2 mmol) in acetone (1 mL) and under nitrogen. After stirring overnight, the reaction mixture was dissolved in water (2 mL) and the solution pH was adjusted (1M NaOH) to 6–8 using pH paper. The solution was then extracted with ethyl acetate (3×5 mL) and the organic layers were stirred for 10 min with $MgSO_4$ and decolorizing carbon. The dried, decolorized extracts were concentrated on a rotary evaporator and the resultant oil was chromatographed on silica gel (J. T. Baker Chemicals, 60–200 mesh, 7 mm×6 cm column, ethyl acetate eluant). The product was obtained as an oil [53 mg, 0.14 mmol, 70% yield, $R_f$ 0.86 (ethyl acetate)] which was crystallized from ether/hexane to afford a pale green, microcrystalline solid (m.p. 64.5°–66.5° C.). In some repeat procedures, the product was somewhat resistant to crystallization (greater concentrations of impurities still present); however, further purification on silica gel using ether/hexane at a 1:1 ratio, ($R_f$ 0.420) provided a product which would crystallize, with a typical final yield ca. 30%. Elemental analysis of DAAA diethylacetal: [found (theory)]: C, 58.90 (58.97); H, 7.29 (7.15); and N, 7.55 (7.64). Molar extinction coefficient (acetone)=4480 at 335 nm. $^1$H NMR (500 MHz, $CDCl_3$) $\delta$:8.55 (d, J=8.4 Hz, 1H, aromatic), 8.27 (d, J=8.5 Hz, 1H, aromatic), 8.25 (d, J=6.8 Hz, 1H, aromatic), 7.58 (t, J=8.2, 1H, aromatic), 7.53 (t, J=7.9, 1H, aromatic), 7.19 (d, J=7.5 Hz, 1H, aromatic), 4.92 (br t, J=5.6 Hz, 1H, NH), 4.22 (t, J=5.6 Hz, 1H, $NCH_2C\underline{H}O$), 3.55–3.45 and 3.30–3.20 (m, 4H, two $C\underline{H}_2CH_3$), 2.99 (d, J=6.0 Hz, 2H, $NCH_2CH$), 2.89 (s, 6H, two $NCH_3$), and 1.06 (t, J=7.1 Hz, 6H, two $CH_2C\underline{H}_3$). DAAA diethyl acetal was dissolved in acetone and aliquots were transferred to a test tube and concentrated under a stream of nitrogen. The tubes were then capped and stored at 5° C. DAAA diethyl acetal (5 $\mu$moles) was activated to DAAA by incubation with 0.1 ml 1N HCl at 4° C. for 12 hours. DAAA solution was neutralized with 0.9 ml of 0.133N NaOH and 0.056M HEPES.

EXAMPLE 2
Flow Cytometry with DAAA.

In an attempt to examine cytosolic ALDH on a single-cell basis, leukemia cell lines and bone marrow cells were incubated with the fluorescent substrate DAAA, washed, and subjected to flow cytometry. The cell lines and plastic nonadherent mononuclear marrow cells were incubated with 50 $\mu$M DAAA at $10^6$ cells/ml for 30 minutes at 37° C. After washing twice, some mononuclear marrow cells were treated with fluorescent monoclonal antibodies (Becton-Dickinson, Mountain View, Calif.), as previously described (M. B. Kastan et al., Blood 74:1517, 1989) to study cytosolic ALDH activity of $CD34^+$, $CD19^+$, and $CD5^+$ marrow cells. The cells were sorted on a Epics 753 Dual Laser Flow Cytometer (Coulter Electronics, Hialeah, Fla.) equipped with two 90-5 water cooled argon lasers (Coherent, Palo Alto, Calif.). Dansyl fluorescence was excited at both 351.1 nm and 363.8 nm using a multiline ultraviolet filter, and was detected at 521 nm. Cytosolic ALDH activity was estimated by the corrected mean fluorescence intensity (MFI) (M. B. Kastan et al., Blood 75:1947, 1990; Kastan, 1989, supra] of dansyl staining, which equals the mean fluorescence of unstained cells subtracted from the mean fluorescence of cells treated with DAAA. The mean fluorescence level represents the average channel value for a given sample on the flow cytometer. To confirm that cellular dansyl fluorescence was the result of the activity of cytosolic ALDH, L1210/CPA cells were incubated with 50 $\mu$M 4-(diethylamino) benzaldehyde (DEAB) for 15 minutes at 37° C. prior to the DAAA incubations to inhibit cytosolic ALDH activity. DEAB is a specific, competitive inhibitor of cytosolic ALDH that is nontoxic to cells in vitro and in vivo. (J. E. Russo et al., Biochem Pharmacol 37:1639, 1988) L1210/CPA cells were also incubated with 50 $\mu$M dansyl glycine (DG) alone (Sigma, St. Louis, Mo.) at $10^6$ cells/ml for 30 minutes at 37° C.

Figure 1E:
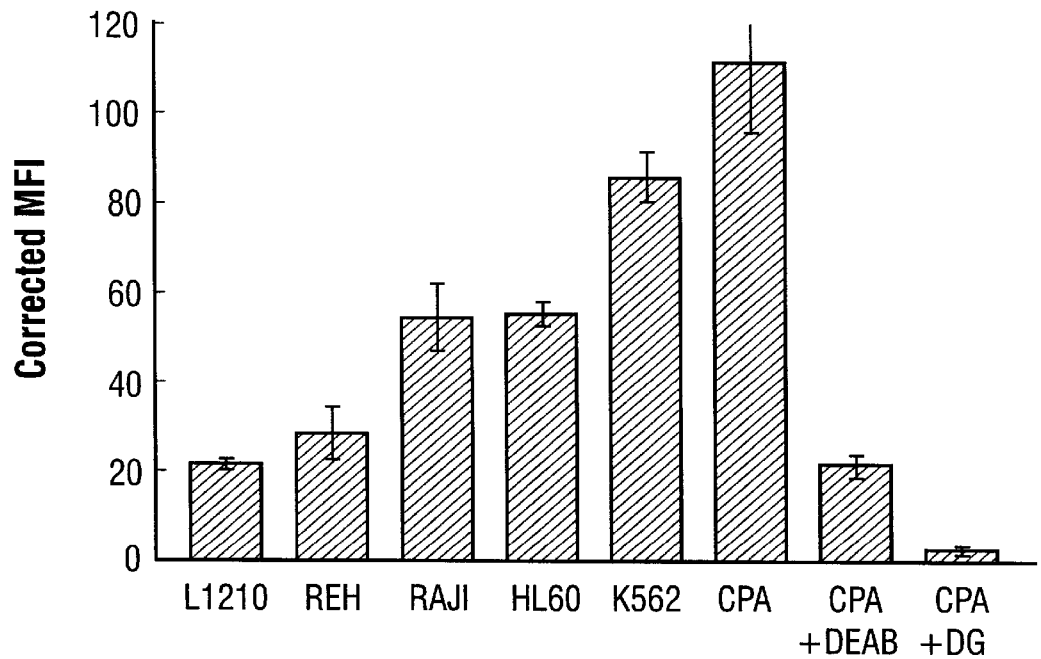
FIG. 1E is a histogram showing corrected mean fluorescence intensity (MFI) for dansyl fluorescence of human and mouse leukemic cell lines treated with DAAA. CPA cells were treated with DEAB or DG. Each data point represents the mean ±S.E.M. of 3–5 separate experiments for each cell line. CPA=L1210/CPA; DG=dansyl glycine.
Figure 2:
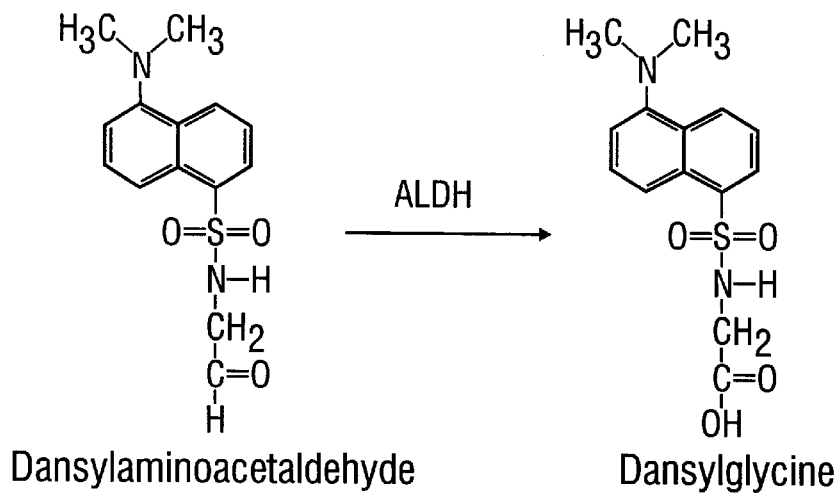
FIG. 2 shows the chemical structures of DAAA and its conversion to dansyl glycine.
Figure 3:
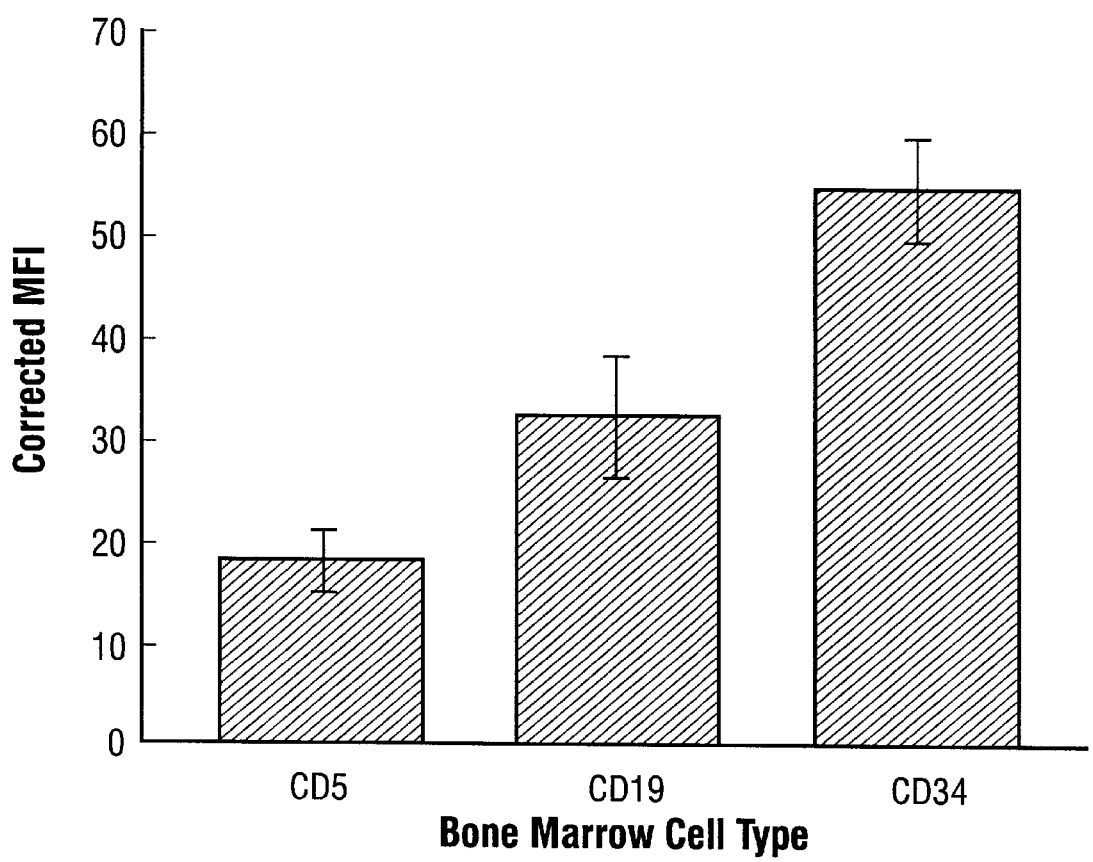
FIG. 3 is a histograph showing corrected MFI for dansyl fluorescence of the indicated selected bone marrow cell subsets treated with DAAA. Each data point represents the mean ±S.E.M. of 3 separate experiments.
Figure 4A:
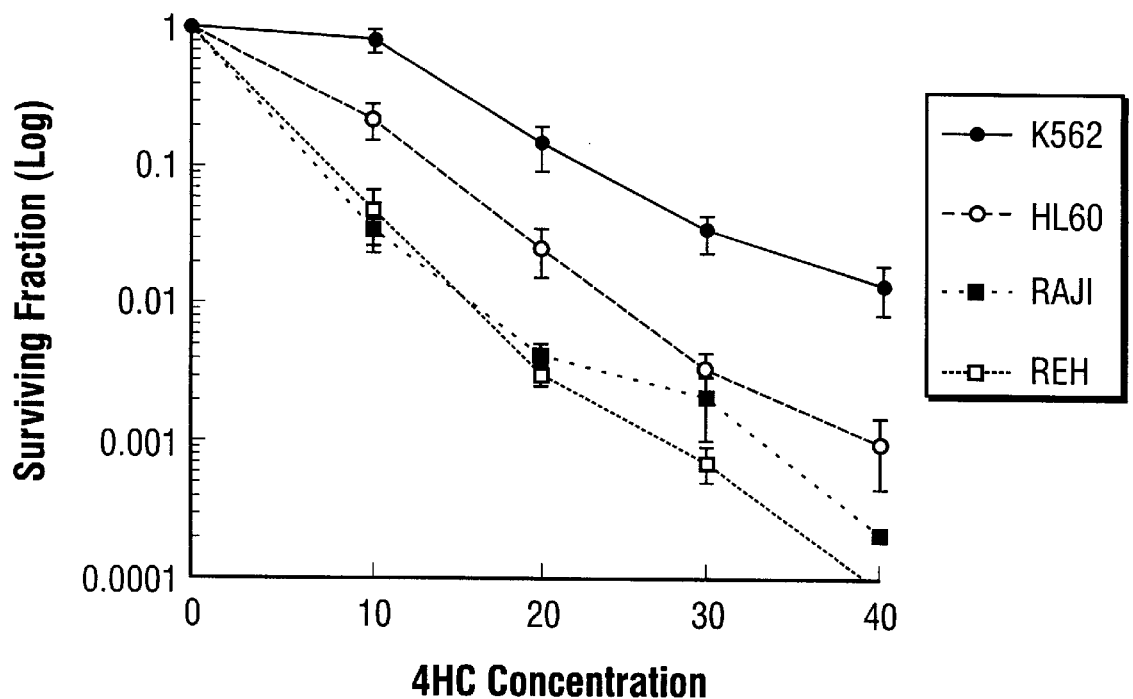
FIGS. 4A and 4B are graphs showing the effect of 4HC on clonogenic leukemia cells. Each data point represents the mean ±S.E.M. of 3–5 separate experiments for each cell line.
Figure 4B:
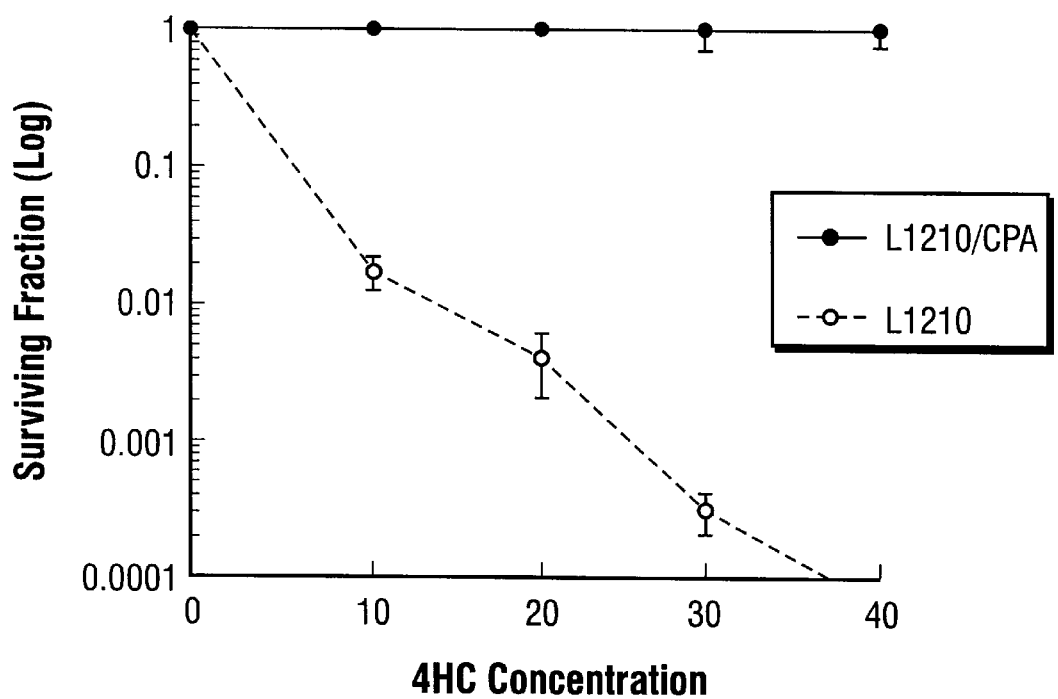

The analysis of the four human leukemia cell lines treated with DAAA is shown in FIGS. 1A–D. This assay is based on the diffusion of hydrophobic DAAA into cells, where subsequent oxidation by ALDH generates dansyl glycine, as shown in FIG. 2. Dansyl glycine contains a carboxylate group that is charged at physiological pH and therefore cannot cross plasma membranes. As shown in FIG. 1E, L1210/CPA cells incubated with dansyl glycine rather than DAAA exhibited no detectable fluorescence. As shown in FIG. 3, $CD34^+$ progenitors also expressed relatively high levels of cytosolic ALDH by DAAA, while lymphocytes, both B ($CD19^+$) and T lineage ($CD5^+$), expressed low levels.

The levels of cytosolic ALDH activity in leukemic cells lines and normal bone marrow cell populations determined by DAAA mirrored the results obtained using cytosolic ALDHh antibodies and flow cytometry (Kastan, 1990, supra). These results indicate that cytosolic ALDH is the enzyme responsible for DAAA oxidation.

DAAA treatment did not appear to harm cells; human bone marrow cells, treated with DAAA and processed by flow cytometry (but not sorted), maintained normal progenitor growth as shown in Table 1 below.

TABLE 1

Growth of bone marrow hematopoietic progenitors isolated by DAAA and flow cytometry

| | Colonies/$10^5$ cells |
|---|---|
| Human CFU-GM | |
| Unstained MNMC | 163 ± 5 |
| Stained MNMC* | 155 ± 5 |
| Dansyl$^+$ MNMC | 216 ± 13 |
| Dansyl$^-$ MNMC | 67 ± 20 |
| Mouse CFU-GM | |
| Dansyl$^+$ | 800 ± 185 |
| Dansyl$^-$ | 250 ± 60 |
| Mouse CFU-S (day 8) | |
| Dansyl$^+$ | 23.5 ± 1 |
| Dansyl$^-$ | 7 ± 1.3 |

MNMC-mononuclear marrow cells
*Incubated with DAAA and processed (but not sorted) by flow cytometry
$^+$ 5% cells with the highest fluorescence
$^-$ 5% of cells with the lowest fluorescence The data in Table 1 show the results of flow cytometry sorting of human and mouse marrow cells based on their fluorescence intensity after incubation with DAAA. The assays of progenitor content is also shown. Isolation of bone marrow cells with high ALDH expression by fluorescence sorting based on DAAA was enriched for hematopoietic progenitors capable of both in vitro and in vivo growth. The 5% of human bone marrow cells with highest dansyl fluorescence produced substantially more CFU-GM than the 5% of cells with lowest dansyl fluorescence ($p=0.007$, T-test). Similarly, using DAAA-derived fluorescence, it was possible to obtain a composition that is enriched for CFU-GM ($p=0.03$) and the more primitive CFU-S ($p=0.01$) from mouse bone marrow.

The foregoing description of the invention is exemplary for purposes of illustration and explanation. It should be understood that various modifications can be made without departing from the spirit and scope of the invention. Accordingly, the following are intended to be interpreted to embrace all such modifications.

EXAMPLE 3

In Vivo Stem Cell Reconstitution of Hematopoietic Repertoire

The unique murine LHSC, that represents about 0.02–0.05% (i.e., 1/2000–1/5000) of mouse bone marrow cells, was isolated. In order to distinguish engraftment due to the transplanted LHSC from engrafting resulting from residual host stem cells, male bone marrow was used as a source of LHSC and female mice were used as the recipients. Small bone marrow cells (about 8–10 μm in diameter) were isolated from bone marrow removed from male mice by counterflow centrifugal elutriation (flow rate 25 ml/min, 3000 rpm–1260 g) or flow cytometry. Cells expressing lineage-specific markers are excluded by fluorescence activated cell sorting (FACS) using a combination of antibodies that recognize these cell surface markers. These cell surface markers included, but were not restricted to the following: CD5 (T-cells), B220 (B-cells), Gr-1 (granulocytes), Mac-1 (monocyte/macrophages), Ter-119 (erythroid). Finally, the small cells lacking these lineage-specific markers and expressing ALDH by DAAA using the technique described above in Example 2 were collected. Ten purified LHSC, along with 20,000 female bone marrow cells that were sorted by counterflow centrifugal elutriation to only be able to provide a transient, early wave of engraftment (Jones, Nature, 347:188, 1990), were injected into lethally irradiated (1100 cGy) "syngeneic" female mice via their tail veins. Peripheral blood or bone marrow was removed from the recipients at various times after transplantation (usually 3, 6, 12, and 18 months after transplantation) and the various lymphohematopoietic lineages were assayed for the Y chromosome (i.e., originating from the transplanted, isolated male LHSC) using a Y chromosome-specific probe and fluorescence in situ hybridization. Bone marrow was isolated from some mice surviving 6–12 months and retransplanted into secondary female recipients as described above. Engraftment in these secondarily transplanted mice was also studied as described above.

The 10 purified male LHSC cells repopulated all lymphohematopoietic lineages of the lethally irradiated female mice for their entire lifetime. In addition, LHSC self-renew as demonstrated by their ability to reconstitute lethally irradiated mice upon secondary serial transplantation. The LHSC are slowly proliferating; they will not form assayable progenitors (CFU-GM, day 8 CFU-S, or day 12 CFU-S) upon primary culture or radio protect (produce early engraftment that will rescue mice from lethal marrow aplasia after total body irradiation). Initial engraftment (occurring in the first month after transplantation) originated from the 20,000 accessory female bone marrow cells capable of only transient, early engraftment. An early wave of engraftment can also be provided by incubating the purified LHSC in a variety of known growth factors in vivo for 7–14 days before transplantation.

Later engraftment (3 months and beyond) occurred primarily from the 10 isolated male LHSC. The LHSC did not express high levels of other presumed stem cell surface markers (c-kit, Sca-1, Thy-1, AA4.1).

What is claimed is:

1. An enriched cellular composition comprising intact, viable human pluripotent hematopoietic stem cells (pluripotent HSCs), wherein the cells of the composition are characterized by:
   a) having a size from about 8 μm to about 10 μm;
   b) expressing levels of aldehyde dehydrogenase as determined from oxidation of dansyl aminoacetaldehyde of from about 10 to about 30 nanomoles aldehyde oxidized/mg protein/min;
   c) being substantially free from expression of markers specific for committed lymphohematopoietic cells; and
   c) being negative for expression of c-kit and Thy-1.

2. The cellular composition of claim 1, wherein no more than about 70% of the pluripotent HSC are CD34 positive and wherein the cells are capable of self-regeneration in a coculture medium and of differentiation to members of the lymphoid hematopoietic lineage.

3. The cellular composition of claim 1, wherein the composition is a cell suspension substantially free of lineage-committed cells.

4. The cellular composition of claim 1, wherein the composition contains fewer than 5% of lineage-committed cells.

5. The cellular composition of claim 1 prepared by preparing a composition enriched in cells that express aldehyde dehydrogenase comprising contacting a cell mixture with dansyl aminoacetaldehyde, and isolating the identified cells by fluorescent cell sorting.

* * * * *